United States Patent [19]

Graham et al.

[11] 4,020,168
[45] Apr. 26, 1977

[54] SUBSTITUTED 2,3-DIHYDRO-1,4-OXATHIIN PLANT GROWTH

[75] Inventors: Bruce A. Graham; Michael A. Puttock, both of Guelph; Ethel E. Felauer, Arkell, all of Canada; Robert W. Neidermyer, Cheshire, Conn.

[73] Assignees: Uniroyal Inc., New York, N.Y.; Uniroyal, Ltd., Ontario, Canada

[22] Filed: Nov. 6, 1975

[21] Appl. No.: 629,731

Related U.S. Application Data

[62] Division of Ser. No. 459,442, April 9, 1974, Pat. No. 3,947,264.

[52] U.S. Cl. .................................. 260/327 P; 71/91
[51] Int. Cl.² ........................................ C07D 327/06
[58] Field of Search .............................. 260/327 P

[56] References Cited

UNITED STATES PATENTS 3,082,214  3/1963  Bluestone ......................... 260/327

OTHER PUBLICATIONS

Marshall, et al., J. Chem. Soc. 1959:2360–2363.

*Primary Examiner*—Natalie Trousof
*Assistant Examiner*—C. M. S. Jaisle

*Attorney, Agent, or Firm*—James J. Long

[57] ABSTRACT

Substituted 2,3-dihydro-1,4-oxathiins of the formula

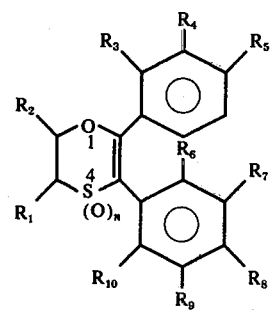

display useful plant growth regulant effects including herbicidal effects. Examples are 2,3-dihydro-5,6-diphenyl-1,4-oxathiin, and 2,3-dihydro-5-(4-methylphenyl)-6-phenyl-1,4-oxathiin 4-oxide. The compounds are useful for the selective control of grasses and as dwarfing agents, as well as for inhibition of vegetative and reproductive axillary growth, and for increasing the sugar content of sugar producing species. A number of these are new compounds.

8 Claims, No Drawings

SUBSTITUTED 2,3-DIHYDRO-1,4-OXATHIIN PLANT GROWTH

This is a division of application Ser. No. 459,442, filed Apr. 9, 1974, now U.S. Pat. No. 3,947,264 issued Mar. 30, 1976.

This invention relates to a method of regulating the growth of plants and to plant growth regulant compositions useful in such method, as well as to chemical compounds useful in such compositions.

Regulation of the growth of plants is frequently desirable for a number of reasons. For example, the control of weeds is of great economic importance. Weed competition inhibits the production of foliage, fruit or seed of agricultural crops. The presence of weeds may also reduce the quality of the harvested crop and reduce harvesting efficiency. Weed control is essential for maximum production of many agronomic and horticultural crops, including corn (*Zea mays L.*), rice (*Oryza sativa L.*) and soybeans (*Glycine max(L.)* Merr.). Weeds on non-cropped areas may cause a fire hazard, undesirable drifting of sand or snow, impaired beauty of the landscape and irritation to persons with allergies. The invention, in one aspect, is based on the discovery that certain substituted 2,3-dihydro-1,4-oxathiins are remarkably effective preemergence herbicides, especially for the selective control of grasses.

Another form of regulation of plant growth that is of great economic importance involves non-herbicidal growth regulant effects. These include, by way of non-limiting example, such effects as dwarfing, antitranspiration, inhibition of vegetative and reproductive axillary growth and increasing the surgar content of sugar producing species. In one important aspect the invention provides a highly effective method for producing such effects, employing certain substituted 2,3-dihydro-1,4-oxathiins.

The substituted 2,3-dihydro-1,4-oxathiins employed to produce herbicidal and other plant growth regulating effects in accordance with the invention are those of the formula

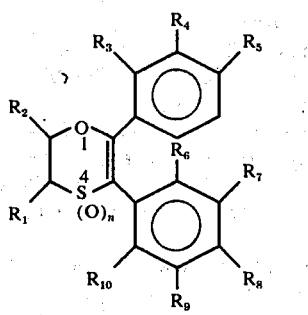

wherein the R's are the same or different and are selected from the group consisting of hydrogen, lower alkyl (especially methyl and ethyl), halogen (e.g., chlorine, bromine, fluorine), lower alkoxy (e.g., methoxy), amino, lower alkylthio (e.g., methylthio), and lower acyloxy (e.g., acetyloxy), and *n* is zero, 1 or 2. The compound wherein all of the R's are hydrogen, and *n* is zero, namely, 2,3-dihydro-5,6-diphenyl-1,4-oxathiin, is known [Marshall and Stevenson, J. Chem. Soc. 2360 (1959)]; the other compounds are believed to be new.

In a preferred class of compounds useful in the invention the R's have the following values:

$R_1 = H$
$R_2 = H, CH_3, C_2H_5$
$R_3 = H, Cl, CH_3$
$R_4 = H, Cl, CH_3$
$R_5 = H, Cl, F, CH_3$

$SCH_3$,
$R_6 = H, Cl, CH_3$
$R_7 = H, Cl, CH_3, OCH_3$
$R_8 = H, Cl, Br, F, CH_3, C_2H_5, OCH_3, NH_2$
$R_9 = H, CH_3$
$R_{10} = H$.

Again, the members of this preferred class of compounds are new, except where all of the R's are hydrogen and *n* is zero (i.e., except for 2,3-dihydro-5,6-diphenyl-1,4-oxathiin).

Of special interest are the compounds of the class described having substituents on one or both phenyls, or a substituent on the dihydro portion of the 1,4-oxathiin ring, or a combination of both. Also of special note are such compounds with a para substituent on the 5-phenyl group.

In one respect, the invention is concerned with chemicals of the kind described wherein *n* is 1 or 2, and use thereof in plant growth regulation.

In another respect the invention is directed to chemicals of the above-stated formula in which at least one of the R's is other than hydrogen or lower alkyl, as well as plant growth regulant uses of such chemicals.

The substituted 2,3-dihydro-1,4-oxathiins employed in the invention may be prepared by reacting a 2-mercaptoalkanol with an appropriately substituted 2-halo-2-phenylacetophenone in the presence of a base and cyclizing the resulting intermediate with water removal in the presence of p-toluenesulfonic acid as a catalyst. The preparation of the 2-halo-2-phenylacetophenones may be achieved using one of the following general procedures:

a. Reaction of a substituted benzoin with thionyl chloride.

b. Reaction of a substituted 2-phenylacetophenone with sulfuryl chloride.

c. Reaction of a substituted 2-phenylacetophenone with bromine. The 2-phenylacetophenones may be prepared by the standard methods known in the literature, such as Friedel-Crafts acylation or Grignard condensation with the appropriate chemicals.

The 2,3-dihydro-1,4-oxathiin in which *n* is zero may be oxidized to the corresponding 4-oxide or 4,4-dioxide (*n* = 1 or 2) by controlled addition of one or two equivalents respectively of a 30% hydrogen peroxide solution to one equivalent of the oxathiin in glacial acetic acid.

In one aspect, the invention contemplates application of any of the substituted 2,3-dihydro-1,4-oxathiin compounds described, in amount effective to regulate growth, to a locus at which such growth regulant effects as preemergence herbicidal effects, dwarfing, fruiting body inhibition, increasing sugar content, etc., are desired. In another aspect, the invention is directed to a plant growth regulant composition comprising a chemical compound as described herein, in amount effective to regulate the growth of plants, in admixture with a carrier therefor. It will be understood that the term plants as used herein includes plant parts such as foliage, roots, flowers and seeds.

The amount of substituted 1,4-oxathiin employed follows conventional practice for herbicidal use or other plant growth regulant uses and the chemical is suitably applied as a formulation in accordance with conventional agricultural chemical practice.

Thus, the chemical may be impregnated on finely-divided or granular inorganic or organic carriers such as attapulgite clay, sand, vermiculite, corn cobs, activated carbon or other granular carriers known to the art. The impregnated granules may then be spread on the soil. Furthermore, the chemical may be formulated, for example, as a wettable powder by grinding it into a fine powder and mixing it with an inactive powdered carrier to which a surface active dispersing agent has been added. Typical powdered solid carriers are the various mineral silicates, e.g, mica, talc, pyrophyllite, and clays. The wettable powder may then be dispersed in water and sprayed on weeds, or the soil surface, or on crop plants. Similarly, an emulsifiable concentrate may be prepared by dissolving the chemical in a solvent such as benzene, toluene, or other aliphatic or aromatic hydrocarbon to which a surface active dispersing agent has been added. The emulsifiable concentrate may then be dispersed in water and applied by spraying. Suitable surface active agents are well known to those skilled in the art, and reference may be had to McCutcheon's Detergents and Emulsifiers, 1970, Allured Publishing Corp., Ridgewood, New Jersey, or Hoffman et al. U.S. Pat. Nos. 2,614,916, cols. 2 to 4 and 2,547,724, cols 3 and 4, for examples of appropriate surface active agents. The concentration of active chemical in the formulation may vary widely, e.g., from 1 to 95%. The concentration of active chemical in dispersions applied to the soil or foliage is almost invariably from 0.002% to 75%. The chemical is frequently applied at rates of 0.10 to 25 pounds per acre. For use as a preemergence herbicide, the chemical is applied to soil which contains weed and crop seed (either to the surface of the soil or incorporated into the upper one to three inches of soil). The chemicals may be employed individually, or as a mixture of two or more chemicals.

The most suitable rate of application in any given case will depend on such factors as the particular response desired, soil type, soil pH, soil organic matter content, wind velocity, the quantity and intensity of rainfall before and after treatment, the air and soil temperature, light intensity and light duration per day. All of these factors can have an influence on the efficacy of the chemicals for a given plant growth control use.

The herbicidal use may include selective weed control in crops such as soybeans, sugar beets, etc.

Depending on crop, variety, dosage, time of application and certain cultural practices, growth regulating effects which are obtained include the following:
a. dwarfing
b. cessation of terminal growth
c. inhibition of axillary and intercalary growth
d. flowering inhibition
e. fruiting body inhibition
f. twisting and epinastic responses
g. modification of root growth
h. increasing sugar in sugar producing species
i. antitranspiration to control water loss.

The foregoing responses are general plant responses any one of which could contribute directly to yield increases. For example, a spray application may be made to tobacco after the flowers are removed to obtain excellent axillary growth control. It may be applied to cotton to facilitate a cut off spray or it may be applied on cotton early to retard the development of rank cotton. Chemicals described herein also may be used on ornamental plants. For example, a spray application may be made to potted chrysanthemums to obtain disbudding which, if done by hand, is very costly. It has been shown to increase the percent sugar in sugarcane. It can be postulated from the results on sugarcane that the chemicals may be preventing breakdown of sugars. The chemicals have also shown remarkable properties in inhibiting flower bud development on peaches. This is useful for preventing frost damage in marginal growth areas where late frosts are inevitable. Flower thinning may be accomplished also.

Another plant growth regulant effect that the chemicals of the invention exhibit is that of antitranspiration. The chemicals control stomatal opening and hence prevent water loss. Due to this response greater yields can be obtained with plants growing under stress.

The following examples, in which all quantities are expressed by weight unless otherwise indicated, will serve to illustrate the practice of the invention in more detail. Examples 1–51 involve preparation of typical plant growth regulant chemicals of the invention, employing four different methods of preparation, identified by the letters A to D in TABLE I, as follows:

A: Halogenation of the appropriate 2-phenylacetophenone followed by reaction with a 2-merceptoalkanol and cyclization.

B: Reaction of a purified 2-halo-2-phenylacetophenone with a 2-mercaptoalkanol followed by cyclization.

C: Oxidation of the appropriate 1,4-oxathiin with one equivalent of oxidizing agent.

D. Oxidation of the appropriate 1,4-oxathiin with two equivalents of oxidizing agent.

The identity of each of the compounds in the working examples was established partly by nuclear magnetic resonance spectrum and party by analytical data. The n.m.r. spectra of the compounds revealed the characteristic couplings due to the protons of the dihydro portion of the dihydro-1,4-oxathiin ring, thereby confirming the structure.

In Examples 52–60 and TABLES II–IX the various substituted 1,4-oxathiins are identified by the Example numbers given in TABLE I.

Preferred new chemicals of the invention are those selected from the group consisting of the chemicals of Examples 3, 4, 2, 20, 21, 22, 9, 10, 6, 12 and 16; especially preferred are the chemicals of Examples 3, 20 and 21.

Plant growth regulant compositions of particular interest containing the present chemicals are those based on chemicals selected from the group consisting of 1, 3, 9, 12, 20, 21, 16, 17, 18, 29, 30 and 38, more preferably those based on chemicals 1, 3, 20, 21 and 12.

For use in preemergence control of weeds the preferred chemicals are those of Examples 3, 20, 21, 30, 38, 10, 16, 18, 13, 24 and 43, more especially the chemicals of Examples 3, 21, 18, 10 and 13.

Preferred plant growth retardant chemicals are those of Examples 1, 20, 29, 30, 38 and 9, more preferably Examples 1 and 20.

For inhibition of axillary vegetative and reproductive growth, preferred chemicals are those of Examples 1, 3, 9, 12, 20, 21, 16, 17 and 18, more preferably 1, 3, 20, 21 and 12.

EXAMPLE 1

Preparation of 2,3-Dihydro-5,6-diphenyl-1,4-oxathiin from 2-phenylacetophenone and 2-Mercaptoethanol. (Method A).

Powdered 2-phenylacetophenone (1021 g., mp. 55–7°) was charged into a three-necked flask equipped with a strong mechanical stirrer, a reflux condenser and a dropping funnel. Sulfuryl chloride (430 ml.) was added in a continuous stream, over 10 minutes, with vigorous stirring. The reaction mixture was kept molten by heating on a steam bath for ½ hour. Benzene (2.5 l.) was added to the reaction mixture and a portion (300 ml.) of the solvent was removed under reduced pressure to remove excess sulfuryl chloride. The reactor was cooled to 20° in an ice bath and a stream of ammonia was bubbled into the solution. After 15 minutes, 2-mercaptoethanol (383 ml.) was added during ½ hour (the reaction mixture temperature remained below 50°). The ammonia sparge was continued for 4 additional hours and the reaction mixture was left at room temperature overnight. A cold solution of hydrochloric acid (1500 ml.). prepared by pouring 37% acid (600 ml.) over crushed ice (900 ml.), was poured into the reactor with stirring. After 15 minutes, stirring was stopped and the reaction mixture separated into two layers. The benzene layer was separated, p-toluenesulfonic acid (20 g.) was added and the reaction mixture was heated under reflux for 4 hours with azeotropic water removal. After cooling, the benzene solution was successively washed with 1.0 N sodium hydroxide solution (1000 ml.), water (500 ml.), filtered, and evaporated under reduced pressure. The warm syrup was then poured slowly into isopropyl alcohol (2.5 l.) with vigorous stirring, left overnight, the solid filtered off, and dried. The light tan coloured product (1062 g., 80% yield) melted at 61°–63° C.

Anal. Calc. for $C_{16}H_{14}OS$: C, 75.57; H, 5.55. Found: C, 75.58; H, 5.74.

EXAMPLE 2

Preparation of 2,3-Dihydro-2-methyl-5,6-diphenyl-1,4-oxathiin from 2-Chloro-2-phenylacetophenone and 1-Mercapto-2-propanol. (Method B)

A mixture of 1-mercapto-2-propanol (19.2 g.) and triethylamine (10.1 g.) in benzene (25 ml.) was added dropwise to a stirred, cooled (20°), solution of 2-chloro-2-phenylacetophenone (23.0 g.) in benzene (200 ml.). The reaction mixture was left at room temperature overnight, washed with water (200 ml.), then with aqueous 5% hydrochloric acid (100 ml.). p-Toluenesulfonic acid (1.0 g.) was added to the benzene solution and the reaction was refluxed for 3 hours with azeotropic water removal. After cooling, the benzene solution was successively washed with 1.0 N sodium hydroxide solution (100 ml.), water (100 ml.) and the benzene removed under reduced pressure. The residue was crystallized from absolute ethanol to give light tan-colored crystals (16 g., 60% yield) melting at 68°–69°.

Anal. Calc. for $C_{17}H_{16}OS$: H, 6.01. Found: C, 76.14, H, 6.05.

EXAMPLE 3

Preparation of 2,3-Dihydro-5,6-diphenyl-1,4-oxathiin 4-oxide from 2,3-Dihydro-5,6-diphenyl-1,4-oxathiin and 30% Hydrogen Peroxide. (Method C)

To a stirred suspension of 2,3-dihydro-5,6-diphenyl-1,4-oxathiin (63.5 g., 0.25 mole) in glacial acetic acid (200 ml.) was added dropwise 30% hydrogen peroxide (30 ml., 0.26 mol). During the addition the temperature of the reaction mixture was maintained below 25° by cooling in an ice bath. After standing for 12 hours at room temperature, the reaction mixture was filtered and the filtrate was poured, with stirring, into water (1400 ml.). The crystalline precipitate was filtered, washed with water, and recrystallized from methanol to give colorless crystals (59.6 g., 88% yield) melting at 157°–9° with decomposition.

Anal. Calc. for $C_{16}H_{14}O_2S$: C, 71.10; H, 5.22. Found: C, 71.22; H, 5.11.

EXAMPLE 4

Preparation of 2,3-Dihydro-5,6-diphenyl-1,4-oxathiin 4,4-dioxide from 2,3-Dihydro-5,6-diphenyl-1,4-oxathiin and 30% Hydrogen Peroxide (Method D)

To a stirred mixture of 2,3-dihydro-5,6-diphenyl-1,4-oxathiin (12.7 g., 0.05 mole), toluene (25 ml.) and formic acid (4 ml.) was added dropwise 30% hydrogen peroxide (12.5 ml., 0.1 mole). The mixture was refluxed on a steam bath for 2 hours, cooled, and the solid product was filtered off. The product was recrystallized from absolute ethanol to give colorless crystals (12.5 g., 87%) melting at 178°–179°.

Anal. Calc. for $C_{16}H_{14}O_3S$: C, 67.12; H, 4.93. Found: C, 66.91; H, 4.93.

EXAMPLES 5–51

Using the procedures of the previous examples and appropriate starting materials, the substituted 1,4-oxathiins shown in TABLE I are prepared. TABLE I gives the systematic name for each product and identifies the method used, and also gives melting point data. In subsequent examples the compounds are identified by the example numbers given in TABLE I.

TABLE I

| Ex. No. | SUBSTITUTED 1,4-OXATHIINS Chemical Name | Method | M.P. (° C) |
|---|---|---|---|
| 1 | 2,3-dihydro-5,6-diphenyl-1,4-oxathiin | A | 61–63 |
| 2 | 2,3-dihydro-2-methyl-5,6-diphenyl-1,4-oxathiin | B | 68–69 |
| 3 | 2,3-dihydro-5,6-diphenyl-1,4-oxathiin 4-oxide | C | 157–159 |
| 4 | 2,3-dihydro-5,6-diphenyl-1,4-oxathiin 4,4-dioxide | D | 178–179 |
| 5 | 2,3-dihydro-6-(4-methylphenyl)-5-phenyl-1,4-oxathiin | B | 86–87 |
| 6 | 2,3-dihydro-6-(4-methylphenyl)-5-phenyl-1,4-oxathiin 4-oxide | C | 155 |
| 7 | 2-(4-chlorophenyl)-5,6-dihydro- | A | 92– |

TABLE I-continued
SUBSTITUTED 1,4-OXATHIINS

| Ex. No. | Chemical Name | Method | M.P. (°C) |
|---|---|---|---|
| | 3-phenyl-1,4-oxathiin | | 94 |
| 8 | 2-(4-chlorophenyl)-5,6-dihydro-3-phenyl-1,4-oxathiin 4-oxide | C | 174–175 |
| 9 | 3-(4-chlorophenyl)-5,6-dihydro-2-phenyl-1,4-oxathiin | A | 68–70 |
| 10 | 3-(4-chlorophenyl)-5,6-dihydro-2-phenyl-1,4-oxathiin 4-oxide | C | 108.5–110 ~140 |
| 11 | 3-(4-chlorophenyl)-5,6-dihydro-2-phenyl-1,4-oxathiin 4,4-dioxide | D | 152–157 |
| 12 | 2-(4-fluorophenyl)-5,6-dihydro-3-phenyl-1,4-oxathiin | A | 80–82 |
| 13 | 2-(4-fluorophenyl)-5,6-dihydro-3-phenyl-1,4-oxathiin 4-oxide | C | 153–154 |
| 14 | 2-(4-fluorophenyl)-5,6-dihydro-3-phenyl-1,4-oxathiin 4,4-dioxide | D | 150–152 |
| 15 | 3-(3-chlorophenyl)-5,6-dihydro-2-phenyl-1,4-oxathiin | A | 65.5–67.5 |
| 16 | 3-(3-chlorophenyl)-5,6-dihydro-2-phenyl-1,4-oxathiin 4-oxide | C | 130–131 |
| 17 | 3-(4-bromophenyl)-5,6-dihydro-2-phenyl-1,4-oxathiin | A | oil |
| 18 | 3-(4-bromophenyl)5,6-dihydro-2-phenyl-1,4-oxathiin 4-oxide | C | 135–136 |
| 19 | 2,3-dihydro-2-methyl-5,6-diphenyl-1,4-oxathiin 4-oxide | C | 145–147 |
| 20 | 2,3-dihydro-5-(4-methylphenyl)-6-phenyl-1,4-oxathiin | A | 75–77 |
| 21 | 2,3-dihydro-5-(4-methylphenyl)-6-phenyl-1,4-oxathiin 4-oxide | C | 145–147 |
| 22 | 2,3-dihydro-5-(4-methylphenyl)-6-phenyl-1,4-oxathiin 4,4-dioxide | D | 172–173 |
| 23 | 3-(4-fluorophenyl)-5,6-dihydro-2-phenyl-1,4-oxathiin | A | 83–85 |
| 24 | 3-(4-fluorophenyl)-5,6-dihydro-2-phenyl-1,4-oxathiin 4-oxide | C | 168 |
| 25 | 3-(4-fluorophenyl)-5,6-dihydro-2-phenyl-1,4-oxathiin 4,4-dioxide | D | 152–153 |
| 26 | 5-(4-aminophenyl)-2-ethyl-2,3-dihydro-6-phenyl-1,4-oxathiin | hydrogenation of corresponding nitro compound | 122–124 |
| 27 | 2,3-dihydro-5-(2-methylphenyl)-6-phenyl-1,4-oxathiin | A | oil |
| 28 | 2,3-dihydro-5-(2-methylphenyl)-6-phenyl-1,4-oxathiin 4-oxide | C | 128–130 |
| 29 | 2,3-dihydro-5-(3-methylphenyl)-6-phenyl-1,4-oxathiin | A | 58–60 |
| 30 | 2,3-dihydro-5-(3-methylphenyl)-6-phenyl-1,4-oxathiin 4-oxide | C | 113.5–115 |
| 31 | 2,3-dihydro-6-[4-(methylthio)phenyl]-5-phenyl-1,4-oxathiin | A | 130–131 135 dec |
| 32 | 3-(2-chlorophenyl)-5,6-dihydro-2-phenyl-1,4-oxathiin | A | 59–61 |
| 33 | 3-(2-chlorophenyl)-5,6-dihydro-2-phenyl-1,4-oxathiin 4-oxide | C | 141–142 |
| 34 | 3-(4-aminophenyl)-5,6-dihydro-2-phenyl-1,4-oxathiin | hydrogenation of corresponding nitro compound | 96–97 |
| 35 | 3-(4-ethylphenyl)-5,6-dihydro-2-phenyl-1,4-oxathiin | A | oil |
| 36 | 3-(4-ethylphenyl)-5,6-dihydro-2-phenyl-1,4-oxathiin 4-oxide | C | oil |
| 37 | 2,3-dihydro-5-(4-methoxyphenyl)-2-phenyl-1,4-oxathiin | A | oil |
| 38 | 2,3-dihydro-5-(4-methoxyphenyl)-6-phenyl-1,4-oxathiin 4-oxide | C | 134–136 |
| 39 | 2-[4-(acetyloxy)phenyl]-5,6-dihydro-3-phenyl-1,4-oxathiin | A | 108–109 |
| 40 | 2-(4-fluorophenyl)-5,6-dihydro-3-(4-methylphenyl)-1,4-oxathiin | A | 70–72 |
| 41 | 3-(3,4-dimethylphenyl)-5,6-dihydro-2-phenyl-1,4-oxathiin | A | 72–73 |
| 42 | 3-(3,5-dimethylphenyl)-5,6-dihydro-2-phenyl-1,4-oxathiin | A | 76–77 |
| 43 | 3-(3,5-dimethylphenyl)-5,6-dihydro-2-phenyl-1,4-oxathiin 4-oxide | C | 143–145 |
| 44 | 2,3-dihydro-5-(3-methoxyphenyl)-6-phenyl-1,4-oxathiin | A | 73–76 |
| 45 | 2-(2-chlorophenyl)-5,6-dihydro-3-phenyl-1,4-oxathiin | A | 71–73 |
| 46 | 2-(3-chlorophenyl)-5,6-dihydro-3-phenyl-1,4-oxathiin | A | 49–50 |
| 47 | 5,6-dihydro-2-(3-methylphenyl)-3-phenyl-1,4-oxathiin | A | oil |
| 48 | 5,6-dihydro-2-(2-methylphenyl)-3-phenyl-1,4-oxathiin | A | 57–58 |
| 49 | 2,3-dihydro-2-methyl-5-(4-methylphenyl)-6-phenyl-1,4-oxathiin | A | oil |

TABLE I-continued

| Ex. No. | SUBSTITUTED 1,4-OXATHIINS Chemical Name | Method | M.P. (° C) |
|---|---|---|---|
| 50 | 2,3-dihydro-2-methyl-5-(4-methylphenyl)-6-phenyl-1,4-oxathiin 4-oxide | C | 150–151 |
| 51 | 3-(4-chloro-3-methylphenyl)-5,6-dihydro-2-phenyl-1,4-oxathiin | A | oil |

EXAMPLE 52

To illustrate effectiveness of the described oxathiins as preemergent herbicides, 600 mg chemical is dissolved in 10 ml organic solvent (e.g., acetone) to which 30 mg conventional emulsifying agent (e.g., isooctylpolyethoxyethanol, "Triton X 100" trademark) is added. The solution is diluted to 100 ml with distilled water. Twenty ml of this 6000 ppm solution is diluted to 250 ppm with distilled water. The chemical is applied at the rate of 10 lbs/A (pounds per acre) by drenching 46 ml of the 250 ppm solution on the surface of soil in 4 ½ inch plastic pots which had been planted with the following weeds: rough pigweed (*Amaranthus retroflexus L.*), purslane (*Portulaca oleracea L.*), tall morningglory (*Ipomea purpurea L. Roth*), crabgrass (*Digitaria ischaemum* (Schreb.)Muhl.), Barnyardgrass (*Echinochloa crusgalli* (L) Beauv.) and giant foxtail (*Setaria faberi Herrm.*). The percent control of the weeds compared to untreated checks is determined two weeks after treatment. TABLE II shows the results with the preemergence herbicides of the invention prepared in accordance with the above examples.

TABLE II

| | Preemergence Herbicides Percent Control of Weeds Including - | | | | | |
|---|---|---|---|---|---|---|
| Ex. | Pig-weed | Purs-lane | Tall M. glory | Bnyd-grass | Crab-grass | Giant Foxtail |
| 1 | 100 | 100 | 0 | 100 | 0 | 0 |
| 3 | 0 | 0 | 0 | 100 | 100 | 100 |
| 20 | 0 | 0 | 75 | 90 | 100 | 95 |
| 21 | 88 | 100 | 100 | 100 | 100 | 100 |
| 22 | 0 | 0 | 0 | 15 | 90 | 75 |
| 28 | 0 | — | 0 | 50 | 95 | 0 |
| 29 | 0 | 0 | 0 | 50 | 95 | 95 |
| 30 | — | — | 0 | 95 | 100 | 100 |
| 38 | 0 | 0 | 0 | 95 | 98 | 100 |
| 9 | 0 | 0 | 0 | 0 | 50 | 50 |
| 10 | 75 | 50 | 40 | 95 | 100 | 100 |
| 15 | 0 | 0 | 0 | 50 | 90 | 10 |
| 16 | 10 | 0 | 0 | 95 | 100 | 95 |
| 17 | 0 | 0 | 0 | 50 | 90 | 10 |
| 18 | 90 | 90 | 0 | 90 | 100 | 98 |
| 12 | 0 | 0 | 0 | 50 | 95 | 25 |
| 13 | 98 | 100 | 0 | 100 | 100 | 100 |
| 23 | 0 | 0 | 0 | 0 | 98 | 100 |
| 24 | 0 | 90 | 0 | 100 | 100 | 100 |
| 25 | 0 | 0 | 0 | 25 | 95 | 100 |
| 40 | 0 | 0 | 0 | 75 | 90 | 100 |
| 43 | 0 | 80 | 0 | 98 | 100 | 100 |
| 2 | 0 | 100 | 0 | 75 | 95 | 90 |
| 19 | 100 | 100 | 0 | 95 | 98 | 95 |

EXAMPLE 53

Selectivity of a herbicide is desirable since it allows control of weeds growing among desirable crop plants. To illustrate the usefulness of the oxathiins of the invention as selective preemergence herbicides, 15 mg chemical is dissolved in 5 ml organic solvent containing 25 mg conventional emulsifying agent (e.g., isooctylpolyethoxyethanol) and this solution diluted to 300 ml with distilled water. The chemical is applied at the rate of 2 lbs/A by drenching the surface of soil containing weed and crop seeds in 6-inch plastic pots with 80 ml of the 50 ppm solution. The percent weed control and crop injury are evaluated two weeks after emergence of the crops. TABLE III illustrates the usefulness of these chemicals as selective preemergence herbicides.

TABLE III

| | Selective Preemergence Herbicide Test | | | | | | | |
|---|---|---|---|---|---|---|---|---|
| | Percent Weed Control | | | | | % Crop Injury | | |
| Ex. | Wild Oats | Wild Mustard | Texas Panicum | Quack grass | Bynd grass | Sugar-beets | Corn | Soy-beans |
| 3 | 80 | 70 | 100 | 100 | 100 | 0 | 10 | 0 |
| 21 | 80 | 85 | 100 | 100 | 100 | 0 | 0 | 20 |

EXAMPLE 54

Listed below are non-limiting examples of formulations which can be prepared with chemicals of this invention.

1. 10.2% active one lb/gallon emulsifiable concentrate
    a. 2,3-Dihydro-5,6-diphenyl-1,4-oxathiin 4-oxide           61.2 g.
    b. Chloroform                                              305.4 g.
    c. *Triton X-114 (trademark; octyl phenoxy poly ethoxy ethanol)  112.2 g.
    d. Toluene                                                 121.2 g.

*other surfactants such as Rohm & Haas's AH861 (trademark), anionic/nonionic blended surfactant, can be substituted 2. 50% active wettable powder
    a. 2,3-Dihydro-6-phenyl-5-(4-methylphenyl-1,4-oxathiin 4-oxide  40.0 g.
    b. Emcol L-72-34 (trademark) sodium dodecyl benzene sulfonate  0.8 g.
    c. Polyfon F (trademark) sodium lignin sulfonate  0.96 g.
    d. Dixie Clay (trademark) Kaolinite clay  9.6 g.
    e. Hi Sil (trademark) hydrated amorphous silicates  28.64 g.

3. 47.3% active 4 lb/gallon emulsifiable concentrate
    a. 5,6-Dihydro-2,3-diphenyl-1,4-oxathiin  24.00 g.
    b. **Triton X-114  5.00 g.
    c. Naphtha  21.79 g.

**other surfactants such as Rohm & Haas's AH861 (trademark) anionic/nonionic blended surfactant can be substituted.

EXAMPLE 55

Four crop species are planted in regular potting medium contained in 12 oz styrofoam cups. The four crops are Pinto Beans — *Phaseolus vulgaris;* Cotton — *Gossypium hirsutum;* Soybeans — *Glycine max* and Wheat — *Triticum aestivum L.* Six hundred mg chemical is dissolved in 10 ml acetone, 1–3 ml toluene and 30 mg of isooctylphenylpolyethoxyethanol (Triton X100; trademark). This mixture is diluted to a volume of 100 ml with distilled water. This mixture contains 6000 ppm active ingredient by weight. The mixture is sprayed to runoff on the four species aforementioned. The plants are sprayed with a DeVilbiss atomizing sprayer, at the following stages of growth.

Pinto — very early first trifoliate p1 Cotton — fully expanded primary leaf stage
Soybeans — first trifoliate nearly expanded Wheat — 2-4 leaf stage Plant growth regulant observations were made from 5 days after spraying throughout the next 3 weeks. These observations included retardation, formative effects and phytotoxicity. These data are presented in TABLE IV, wherein "retd" stands for retardation, "phyto" stands for phytotoxicity, "N.G." stands for new growth, "trif" stands for trifoliate, and "n.e." stands for no effect.

TABLE IV

| Ex. | Bean | Plant Growth Regulation Cotton | Soybean | Wheat |
|---|---|---|---|---|
| 1 | 90% retd | 30% retd | 20% retd | 20% phyto |
| 3 | n.e. | 10% phyto | 35% phyto | |
| 5 | n.e. | 10% phyto | 10% phyto | 50% phyto |
| 6 | n.e. | N.G. sl. deformed and chlorotic | slight puckering | 10% phyto |
| 20 | 20% retd | 80% terminal growth retarded | 80% N.G. retd | 20% retd |
| 21 | n.e. | Trifoliates severely retd | N.G. severely epinastic | 30% retd darker green |
| 22 | n.e. | n.e. | 30% retd | 5% phyto |
| 27 | Trifoliate retd | 25% phyto | 75% phyto | 50% phyto |
| 28 | n.e. | 20% phyto | 30% retd | n.e. |
| 29 | Trifoliate 50% retd | N.G. 60% retd | 60% retd | 10% phyto |
| 30 | 20% retd | N.G. 60% retd | 60% retd | n.e. |
| 35 | N.G. 50% retd | N.G. 60% retd | 50% retd dark green | n.e. |
| 36 | Trif 75% retd | N.G. 60% retd | 85% phyto | — |
| 37 | N.G. 50% retd | N.G. 80% retd | 20% retd | — |
| 38 | 60% retd dark green | N.G. 20% retd | 30% retd | 60% retd dark green |
| 7 | 75% retd | N.G. 30% retd forced terminal growth | sl epinasty | 20% phyto |
| 8 | n.e. | sl epinasty | N.G. epinasty | 10% phyto |
| 9 | Trif 100% | 100% retd | 80% retd | n.e. |
| 10 | n.e. | Trif retd | 80% retd | 80% retd |
| 32 | Trif 80% retd | sl epinasty | 30% retd dark green | 5% phyto |
| 33 | n.e. | 5% phyto | N.G. 60% retd dark green | n.e. |
| 15 | 10% phyto | terminal 80% retd | 30% retd 100% phyto | 10% phyto |
| 16 | 20% retd | Terminal 80% retd | N.G. 100% retd | 20% retd |
| 17 | n.e. | 80% retd term stopped | 100% retd | 20% retd |
| 18 | 30% retd | Terminal 80% retd | 80% retd | 30% retd |
| 12 | 10% phyto | N.G. 60% retd | N.G. 100% retd | 15% phyto |
| 13 | n.e. | N.G. 30% retd | 60% retd dark green | 30% retd dark green |
| 23 | n.e. | 20% phyto | Terminals 60% retd | 20% retd |
| 24 | n.e. | Terminal 30% retd | 60% retd | 20% retd |
| 25 | n.e. | n.e. | 30% retd & dark green | n.e. |
| 40 | n.e. | N.G. 50% retd | N.G. 80% retd | 30% retd dark green |
| 41 | n.e. | 50% retd | 20% phyto | 15% phyto |
| 43 | n.e. | N.G. 30% retd | n.e. | n.e. |
| 2 | n.e. | n.e. | 80% retd | 10% retd |
| 19 | 60% retd | N.G. 30% retd | 60% retd | 60% retd |
| 45 | 75% retd | N.G. mod puckered | 60% retd | n.e. |
| 46 | N.G. 35% retd | N.G. 95% killed | 80% retd | n.e. |
| 47 | N.G. dark green | N.G. 95% killed | 40% retd | n.e. |
| 48 | N.G. dark green | N.G. 90% killed | 40% retd | n.e. |
| 51 | N.G. 80% retd | 30% retd | 50% retd | n.e. |

EXAMPLE 56

To further illustrate the utility of these chemicals, data are presented in this Example on the growth retarding properties of soybeans (Corsoy variety). Seventy-five mg chemical is dissolved in 10 ml acetone, 2 ml toluene and 30 mg of Triton X100 (isooctyl phenyl poly ethoxyethanol). This mixture is diluted to a 50 ml volume with distilled water. This mixture is equivalent to 1500 ppm. In some cases a lower rate of 750–800 ppm is used, thus only 38–40 mg are used respectively for the mixture. This mixture is sprayed to runoff on three pots each containing two soybean plants in the early first trifoliate leaf stage. The spray is applied with a DeVilbiss atomizing sprayer. The first height measurement is taken at spraying time and the second when the control plants began to pod or approximately four weeks after spraying. A percent growth figure is obtained by using the following formula $$\% \text{ Retardation} = \frac{G.C. - G.T.}{G.T.} \times 100$$

where G.C. stands for growth of control plants in cm, and G.T. stands for growth of treated plants. TABLE V shows the unique growth retarding properties of the chemicals on soybeans.

TABLE V

| Ex. | Soybean Retardation Rate PPM | % Retardation |
|---|---|---|
| 1 | 750 | 76 |
| 20 | 750 | 90 |
| 21 | 750 | 67 |
| 6 | 750 | 57 |
| 9 | 1500 | 36 |
| 10 | 1500 | 37 |
| 17 | 1500 | 30 |
| 18 | 1500 | 39 |
| 28 | 800 | 52 |
| 29 | 800 | 58 |
| 30 | 800 | 82 |
| 37 | 1500 | 13 |
| 38 | 1500 | 76 |

EXAMPLE 57

The unique property of these chemicals to inhibit axillary growth is exhibited in this Example. Four hundred mg chemical is dissolved in 10 ml solvent (e.g., toluene, acetone, or mixture thereof) containing 3% surfactant (e.g., isooctylphenylpolyethoxyethanol [Triton X$\phi$; trademark], polyoxyethylene sorbitan monolaurate [Tween 20; trademark] or AH831 [trademark] blend of anionic and nonionic surfactants). This mixture, diluted to 100 ml with distilled water, is equivalent to 4000 ppm chemical. Lower dosages may be made by diluting the 4000 ppm formulation or by dissolving less chemical in the solvent mixture. Twenty ml of one of the mixtures described above is sprayed on tobacco plants (Nicotiana tabacum Xanthii variety) at the early flowering stage, but with flowers removed to force axillary growth. The spray is directed to the terminal growing areas in order to facilitate wetting each node as the mixture runs down the central stalk. Percent sucker control data are calculated on the green weight of the suckers which are plucked approximately four weeks after spray application. The following formula is used to calculate percent sucker control: t,360 where S.W.C. stands for sucker weight in grams for the control and S.W.T. stands for sucker weight in grams for the treated plant. TABLE VI shows the unique ability of the chemicals to inhibit sucker or axillary bud growth.

TABLE VI

| Ex. | SUCKER CONTROL Rate PPM | % Axillary Bud Control |
|---|---|---|
| 1 | 4000 | 99 |
| 3 | 1000 | 88 |
| 9 | 4000 | 91 |
| 10 | 4000 | 68 |

TABLE VI-continued

| Ex. | SUCKER CONTROL Rate PPM | % Axillary Bud Control |
|---|---|---|
| 12 | 4000 | 100 |
| 13 | 4000 | 80 |
| 20 | 3000 | 99 |
| 21 | 3000 | 99 |
| 6 | 3000 | 63 |
| 30 | 4000 | 77 |
| 15 | 3000 | 76 |
| 16 | 3000 | 99 |
| 17 | 3000 | 95 |
| 18 | 3000 | 91 |

EXAMPLE 58

To explain more clearly the activity of this invention on flowering, the following test on chrysanthemum is described. A sprayable formulation is made by emulsifying 1.06 g of a 4 lb active gallon (see Example 54 formulation 3 for composition) containing 2,3-dihydro-5,6-diphenyl-1,4-oxathiin and diluting this mixture to 100 ml volume with water. This mixture is equivalent to 5000 ppm. A respective dosage of 2500 is made by diluting the 5000 ml emulsion. This sprayable formulation is applied to Fred Shoesmith mums that had been exposed to 16 and 23 Short Days (10 hours) to induce flowering. The spray is applied to runoff with a DeVilbiss atomizing sprayer. The plants are placed back in the growth chamber until the total short day period of six weeks is completed. They are then removed and placed in a greenhouse until flowering. Data are taken by counting the number of axillary flower buds one-half inch or longer below the terminal flower. These data are presented in TABLE VII. The date in TABLE VII illustrate the unique properties of this invention in reducing the number of flower buds that would ordinarily require hand removal.

TABLE VII

| Treatment | Chrysanthemum Flowering | | Average Axillary Flower Buds Per Plant |
|---|---|---|---|
| | Rate PPM | Spray Timing | |
| Ex. I Chem. | 5000 | 16 days after first 10-hour day | 4.5 |
| | 2500 | first 10-hour day | 5.3 |
| | 5000 | 23 days after first 10-hour day | 4.0 |
| | 2500 | first 10-hour day | 5.9 |
| Checks | | | 12.0 |

EXAMPLE 59

To illustrate further the growth regulating properties of the chemicals on the metabolic activity of plants, 45.6 cc of chemical (formulated as a four pound active gallon — see Example 54 formulation 3 for composition) were brought up to an 1892 ml volume with water. This solution was applied at a 3 lb per acre rate in 30 gallons of water to sugarbeets, Beta vulgaris, 3 weeks before harvest.

The yield data were determined by hand harvesting each of three treatment replicates which consisted of one row 15 feet long. The sugar content was determined by measuring the sucrose content of beets that were randomly selected from each plot.

The data are given in TABLE VIII illustrating the increase in sugar content due to the chemical application. Based on an average yield of 40,000 pounds of sugar per acre, the one percent increase would add 400 pounds of extra sugar per acre.

TABLE VIII

SUGAR INCREASE

| Treatment | Rate (lbs/A) | Sugar (%) |
|---|---|---|
| Ex 1 Chem. | 3 | 16.08 |
| Ex 1 Chem. | 1½ | 15.62 |
| Check | | 15.05 |

EXAMPLE 60

To illustrate further the unique growth regulating properties of the chemicals on flowering, 8.5 g. of the chemical of EXAMPLE 1 (formulated as a four pound active gallon — see EXAMPLE 54 for composition) was brought up to a 400 ml volume with water. This emulsion was applied to four replicate branches of Red Haven peaches that were in the second year of bearing. The flower buds at this time were in the tight bud stage. The chemical emulsion was applied to the branches to the point of run off, with a ½ inch brush. The buds were counted and recorded for each branch. Each branch had an average of 35 flower buds. The number of flower buds open were counted 28 and 33 days after application and compared to the original bud count. The percent flowers open figure was established from these two counts, with the results shown in TABLE IX.

A peach farmer is often faced with yield losses due to late frost. The chemicals herein described inhibit flower opening and hence flower kill.

TABLE IX

INHIBITION OF FLOWER OPENING

| | | Percent Flowers Open | |
|---|---|---|---|
| Chemical | Rate PPM | 28 days after Application | 33 days after Application |
| Ex. 1 | 10,000 | 10.2 | 17.6 |
| | 5,000 | 64.3 | 91.6 |
| | 2,500 | 62.5 | 100.0 |
| Check | | 80.0 | 100.0 |

We claim:
1. A chemical selected from the group consisting of 2,3-dihydro-5,6-diphenyl-1,4-oxathiin 4-oxide, 2,3-dihydro-5-(4-methylphenyl)-6-phenyl-1,4-oxathiin, 2,3-dihydro-5-(4-methylphenyl)-6-phenyl-1,4-oxathiin 4-oxide, 2,3-dihydro-5-(3-methylphenyl)-6-phenyl-1,4-oxathiin 4-oxide, 2,3-dihydro-5-(4-methoxyphenyl)-6-phenyl-1,4-oxathiin 4-oxide, 3-(4-chlorophenyl)-5,6-dihydro-2-phenyl-1,4-oxathiin 4-oxide, 3-(3-chlorophenyl)-5,6-dihydro-2-phenyl-1,4-oxathiin 4-oxide, 3-(4-bromophenyl)-5,6-dihydro-2-phenyl-1,4-oxathiin 4-oxide, 2-(4-fluorophenyl)-5,6-dihydro-3-phenyl-1,4-oxathiin 4-oxide, 3-(4-fluorophenyl)-5,6-dihydro-2-phenyl-1,4-oxathiin 4-oxide and 3-(3,5-dimethylphenyl)-5,6-dihydro-2-phenyl-1,4-oxathiin 4-oxide.
2. A chemical as in claim 1 which is 2,3-dihydro-5,6-diphenyl-1,4-oxathiin 4-oxide.
3. A chemical as in claim 1 which is 2,3-dihydro-5-(4-methylphenyl)-6-phenyl-1,4-oxathiin 4-oxide.
4. A chemical as in claim 1 which is 3-(4-bromophenyl)-5,6-dihydro-2-phenyl-1,4-oxathiin 4-oxide.
5. A chemical as in claim 1 which is 3-(4-chlorophenyl)-5,6-dihydro-2-phenyl-1,4-oxathiin 4-oxide.
6. A chemical as in claim 1 which is 2-(4-fluorophenyl)-5,6-dihydro-3-phenyl-1,4-oxathiin 4-oxide.
7. A chemical as in claim 1 which is 2,3-dihydro-5-(4-methylphenyl)-6-phenyl-1,4-oxathiin.
8. 2,3-Dihydro-2-methyl-5,6-diphenyl-1,4-oxathiin 4-oxide.

* * * * *